United States Patent [19]
Cleveland et al.

[11] Patent Number: 5,682,264
[45] Date of Patent: *Oct. 28, 1997

[54] UNIVERSAL MICROSCOPE DRAPE

[75] Inventors: John T. Cleveland; Benjamin M. Rubin, both of Jacksonville, Fla.

[73] Assignee: Microtek Medical, Inc., Columbus, Miss.

[*] Notice: The term of this patent shall not extend beyond the expiration date of Pat. No. 5,467,223.

[21] Appl. No.: 22,662

[22] Filed: Mar. 1, 1993

[51] Int. Cl.$^6$ .......................... G03B 11/04; B65D 85/38
[52] U.S. Cl. .................. 359/510; 359/511; 206/316.1
[58] Field of Search ........................ 359/503, 506, 359/507, 510, 513, 808–810, 815, 819, 827, 894, 900; 206/316.1

[56] References Cited

U.S. PATENT DOCUMENTS

| | | | |
|---|---|---|---|
| 3,133,140 | 5/1964 | Winchell | 359/511 |
| 4,266,663 | 5/1981 | Geraci | 359/510 |
| 4,799,779 | 1/1989 | Mesmer | 359/510 |
| 4,807,594 | 2/1989 | Chatenever | 359/513 |
| 5,155,624 | 10/1992 | Flagler | 359/510 |
| 5,311,358 | 5/1994 | Pederson et al. | 359/510 |
| 5,467,223 | 11/1995 | Cleveland et al. | 359/510 |

*Primary Examiner*—Thong Nguyen
*Attorney, Agent, or Firm*—Baker & Botts, L.L.P.

[57] ABSTRACT

The universal microscope drape is based on a positioning system that includes a different adapter member for each differently manufactured microscope and a universal positioning member of a microscope drape that engages each different adapter member. The microscope drape positioning member is attached to the microscope drape cover member to position the microscope drape cover member in a predetermined orientation on the microscope. The adapter member is interchangeable with a lens unit that is detachably secured to a microscope. The lens unit, upon removal, is joined to the adapter member to permit resecurement of the lens unit to the microscope when the adapter member is joined to the microscope. Since the adapter member has a universal engagement portion that is engagable with the universal positioning member of the microscope drape, the same microscope drape can be used to cover differently manufactured microscopes of the same general size and shape.

8 Claims, 3 Drawing Sheets

UNIVERSAL MICROSCOPE DRAPE

BACKGROUND OF THE INVENTION

This invention relates to microscope drapes and more particularly to a novel positioning system for microscope drapes that permits use of a universal drape on a variety of different surgical microscopes.

Microscopes used for surgery are generally permanent fixtures in an operating room, and cannot be easily sterilized each time a surgery is performed. Thus it is common practice to cover a surgical microscope and any associated support structure with a disposable sterile covering or drape that is replaced as needed, normally for each surgical procedure.

The microscope drape is usually initially affixed to a particular portion of the microscope, such as the lens housing for the objective lens, to orient the drape with respect to other microscope structure. For example, a microscope drape such as shown in U.S. Pat. No. 4,799,779 includes an annular positioning sleeve attached to a cover member of the drape. The positioning sleeve is adapted to fit onto the objective lens housing of the microscope as an initial location point for the microscope drape. Once the microscope drape is attached to the objective lens housing, other portions of the drape can be conveniently spread and positioned to cover the remainder of the microscope.

To ensure that the microscope drape forms a sterile barrier between the microscope and the operating room, it is desirable that the positioning sleeve tightly grip the objective lens housing and that other portions of the microscope drape including the cover member be arranged on the microscope as a protective enclosure.

It has been found that a microscope drape positioning sleeve that tightly grips the lens housing of one microscope may not tightly grip the lens housing of a similar size microscope made by another manufacturer. If an ill fitting positioning sleeve slips away from the objective lens housing during surgery, it may impede the surgeon's view or necessitate interruption of the surgery to resecure the positioning sleeve.

Thus, to ensure compatibility between the microscope and the microscope drape, it is customary to manufacture microscope drapes with positioning sleeves of different size to provide size correspondency with the lens housings of differently manufactured microscopes.

Thus, manufacturers of microscope drapes, and hospitals which stock such microscope drapes, must keep separate inventories of microscope drapes for each differently manufactured microscope that is used in a surgical facility.

If there is an unexpected depletion of microscope drapes for a microscope of one manufacturer and an abundance of drapes for a microscope of another manufacturer, it is normally not feasible to interchange such drapes because of the different positioning sleeves needed for each different microscope lens housing. An operating room may thus be rendered unusable until an appropriate drape for the microscope is obtained.

It is therefore desirable to provide a positioning system for a microscope drape that permits use of the same microscope drape with the same positioning sleeve on a variety of different microscopes having different lens housings.

OBJECTS AND SUMMARY OF THE INVENTION

Among the several objects of the invention may be noted the provision of a novel microscope drape, a novel microscope drape positioning system, a novel microscope drape positioning system that permits use of a universal drape for a variety of microscopes of different manufacturers, and a novel method of draping a microscope.

Other objects and features of the invention will be in part apparent and in part pointed out hereinafter.

In accordance with the present invention, the microscope drape positioning system is directed to microscopes having objective lens housings with detachable lens units.

The detachable lens unit, which is usually threaded to the objective lens housing of the microscope, is interchanged with an adapter member having the same threads as the lens unit. The adapter member is also provided with threads that permit the removed lens unit to be joined to the adapter member. The removed lens unit can thus be resecured to the microscope lens housing via the adapter member, in a functional viewing position.

The adapter member is also formed with a universal engaging portion that joins with a complementary shaped universal engaging portion of a microscope drape positioning member.

In a preferred embodiment of the invention, the engagement portion of the adapter member is in the form of an outer surface of a frustum of a cone and the complementary engagement portion of the microscope drape positioning member is in the form of an inner surface of a hollow frustum of a cone. The inner frustum surface of the drape positioning member is mounted upon the outer frustum surface of the adapter member to form a secure but detachable joint.

Since the microscope drape positioning member is not directly attached to the objective lens housing, there is no need for compatibility between the microscope drape positioning member and the objective lens housing.

In accordance with the invention, each differently manufactured microscope is provided with its own compatible adapter member. Thus there may be a different adapter member for microscopes of each different manufacturer. However, each different adapter member is formed with the same engagement portion to mate with the same corresponding engagement portion of the microscope drape positioning member.

Thus the adapter member for each differently manufactured microscope is formed with a universal engagement portion that mates with the universal engagement portion of a universal positioning member of a microscope drape. Since the universal positioning member of the microscope drape is matched to the universal engagement portion of each different adapter member, a universal microscope drape with the universal positioning member can be used to cover a variety of differently manufactured microscopes of the same general size and shape regardless of any differences in the lens housings of such microscopes.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figure 1:
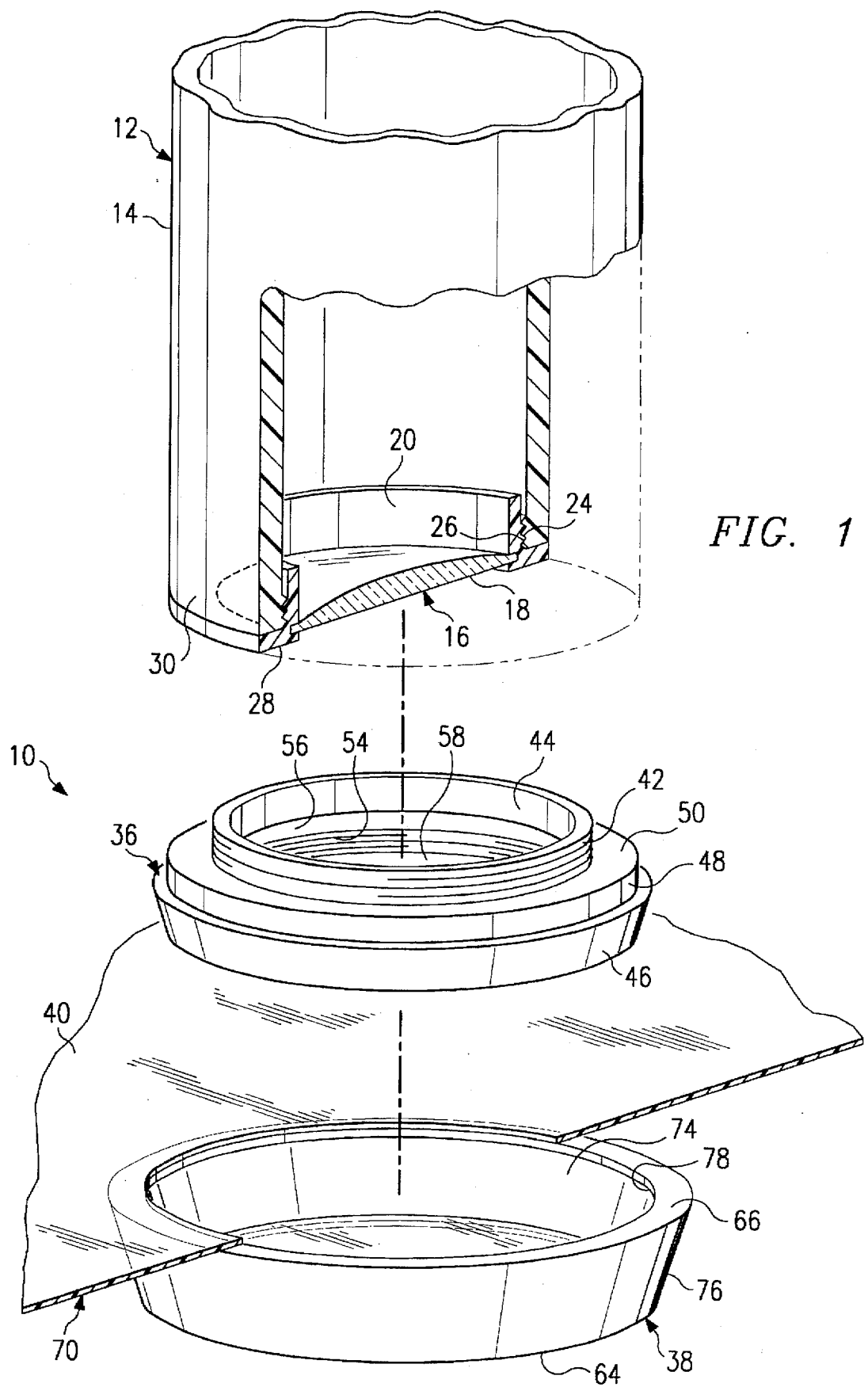
FIG. 1 is an exploded perspective view of a positioning system for a microscope drape, incorporating one embodiment of the invention, prior to installation on a microscope.
Figure 2:
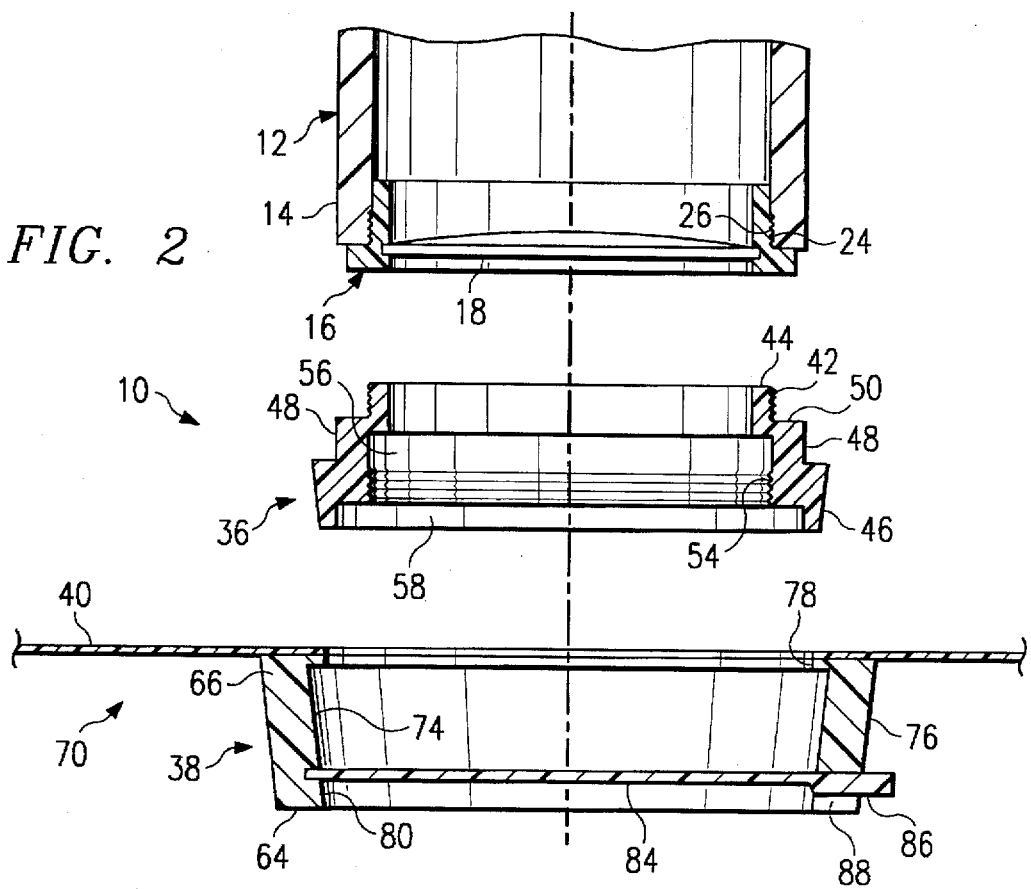
FIG. 2 is an exploded sectional view of the component parts shown in FIG. 1.
Figure 3:
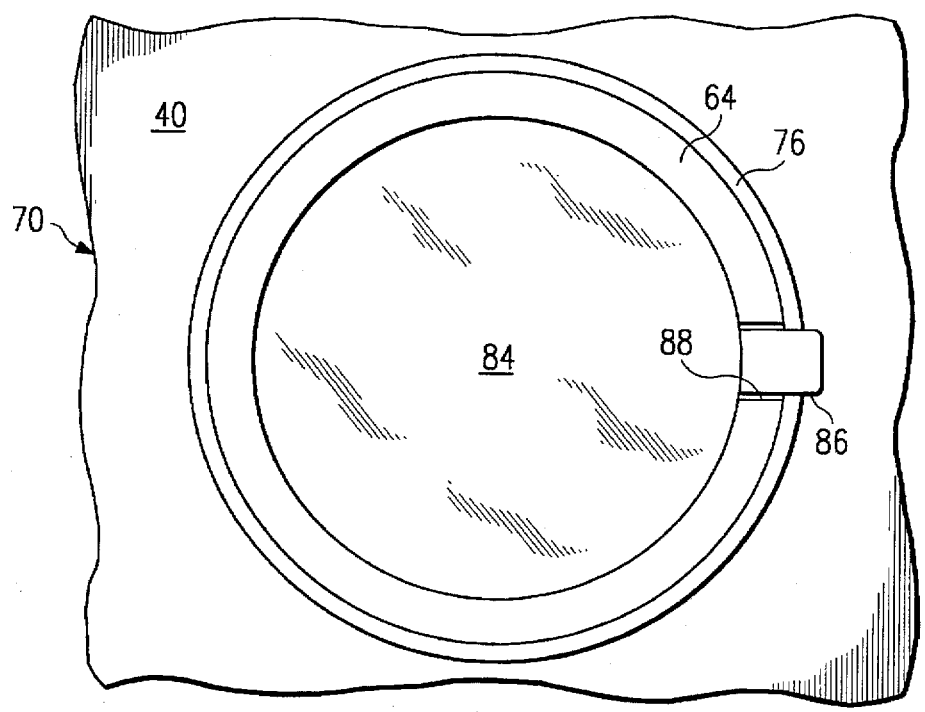
FIG. 3 is a plan view of the microscope drape.
Figure 4:
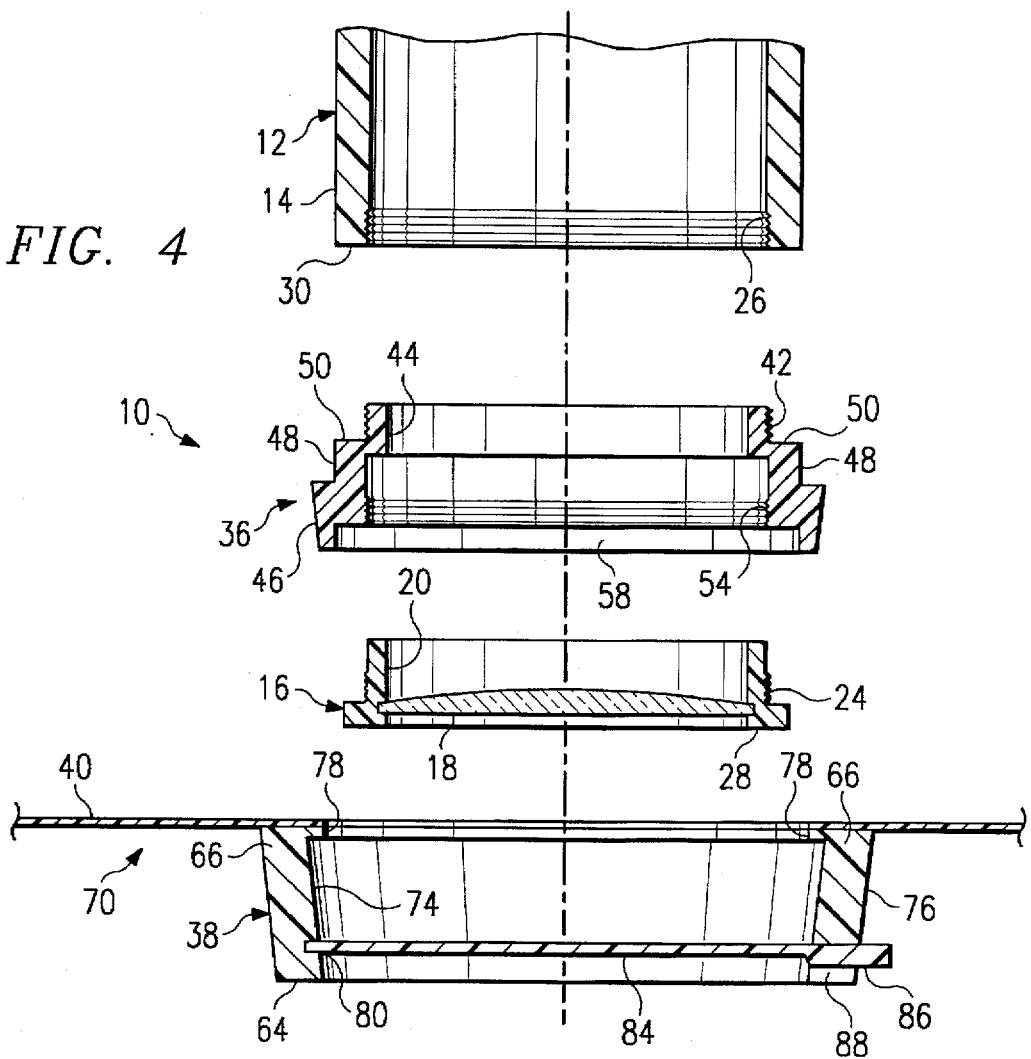
FIG. 4 is an exploded sectional view of the installed system.

A positioning assembly for microscope drapes incorporating a best mode and preferred embodiment of the invention is generally indicated by the reference number 10 in FIGS. 1 and 2.

The positioning assembly 10 is adapted for use on a microscope 12 having an objective lens unit housing 14 of hollow cylindrical form which contains a detachable lens unit 16. The microscope 12 is a surgical microscope of known construction, such as shown in U.S. Pat. No. 4,799,779, the details of which are not necessary for an understanding of the invention, and have been omitted for purposes of simplicity.

The lens unit 16 includes an objective lens piece 18 affixed to an annular lens collar 20. The lens collar 20 is formed with exterior threads 24 that interengage with interior threads 26 formed on the lens unit housing 14. The lens unit 16 further includes a stop flange 28 that is engagable with an end portion 30 of the lens unit housing 14.

The positioning assembly 10 includes an adapter member 36 and a drape positioning member 38. The drape positioning member 38 is attached to a microscope drape cover member 40.

The adapter member 36 is in the form of a ring having exterior and interior steps and is preferably formed of a rigid material such as aluminum. An exterior thread 42 is formed at an end rim 44 of the adapter member 36 identical to the exterior thread 24 of the lens unit 16. The exterior thread 42 is thus engagable with the interior thread 26 of the lens unit housing 14. The inner diameter of the rim portion 44 is substantially the same as the inner diameter of the lens collar 20.

An exterior tapered surface 46 is formed at an opposite end portion of the adapter member 36. The tapered surface 46, also referred to as a universal engaging surface, is in the form of a frustum of a cone and has an angle of taper between 15° and 22°, preferably 18.4°. An exterior step 48 of the adapter member 36 is formed between the threads 42 and the tapered surface 46. The step 48 includes a stop surface 50.

The interior portion of the adapter member 36 is formed with an interior thread 54 identical to the interior thread 26 of the lens unit housing 14. The interior thread 54 is thus engagable with the exterior thread 24 of the lens unit 16. An interior clearance space 56 is provided between the interior thread 54 and the rim portion 44.

The annular member 36 further includes an annular recess 58 proximate the threads 54 having a diameter larger than the outer diameter of the stop flange 28 of the lens unit 16.

The microscope drape positioning member 38 is in the form of a hollow frustum of a cone, and is preferably formed of a soft, flexible and deformable thermoplastic rubber material such as sold under the trademark Krayton®, manufactured by Shell Chemical Co. The positioning member 38 includes a minor base end 64 and an opposite major base end 66. The microscope drape cover member 40, which is formed of a relatively thin transparent plastic material such as polyethylene, polypropylene or other suitable polymer or copolymer film, is joined to the positioning member 38 in any suitable known manner such as by bonding to the major base end 66 by heat welding for example. A microscope drape 70 which incorporates the positioning member 38 and the cover member 40 is of any suitable size and shape to cover the microscope 12.

A tapered inner surface 74 of the positioning member 38 is in the form of a conical frustum and has a taper angle that corresponds to the taper angle of the universal engagement surface 46 of the adapter member 36.

The tapered inner surface 74, also characterized as a universal engaging surface, is sized to frictionally receive the universal outer engaging surface 46 of the adapter member 36.

An outer surface 76 of the positioning member is also in the form of a frustum of a cone and is substantially parallel to the inner surface 74. A lip portion 78 is formed at the major base end 66 and an annular groove 80 is formed in the tapered inner surface 74 proximate the minor base end 64, to receive a transparent plastic lens 84. The lens 84 includes a handle extension 86 that is aligned with a recess 88 at the minor base end 64.

In using the positioning assembly 10 for the microscope 12, the lens unit 16 is interchanged with the adapter member 36. The lens unit 16 is thus unthreaded from the lens unit housing 14 and replaced by the adapter member 36. The exterior threaded portion 42 of the adapter member 36 is thus engaged with the interior threaded portion 26 of the lens unit housing 14. If desired, the adapter member 36 can be threaded to the lens housing 14 until the stop surface 50 engages the end portion 30 of the lens unit housing 14.

The removed lens unit 16 is joined to the adapter member 36 by engaging the outer threaded portion 24 of the lens unit 16 with the inner threaded portion 54 of the adapter member 36. If desired, the lens unit 16 can be threaded until the flange 28 seats in the recess 58 of the adapter member 36. The recess 58 is sized to permit peripheral access to the flange 28. If desired, the depth of the recess 58 can be narrower than the thickness of the flange 28 to facilitate insertion and removal of the lens unit 16 from the adapter member 36. The lens unit 16 is thus held in relation to the lens unit housing 14 by the adapter member 36.

The microscope drape 70, which includes the drape positioning member 38 and the drape cover member 40, can then be installed on the microscope 12. This is accomplished by aligning the positioning member 38 with the previously installed adapter member 36 and the resecured lens unit 16. The positioning member 38 is mounted onto the adapter member 36 such that the inner tapered surface 74 embraces and grips the outer tapered surface 46 of the adapter member 36.

The plastic lens 84 is thus aligned with the lens piece 18 of the lens unit 16 to provide a clear field of view from the microscope 12. If desired, the plastic lens 84 can be removed from the positioning member 38 by pushing the tab portion 86 of the lens 84 away from the minor base end 64.

Figure 5:
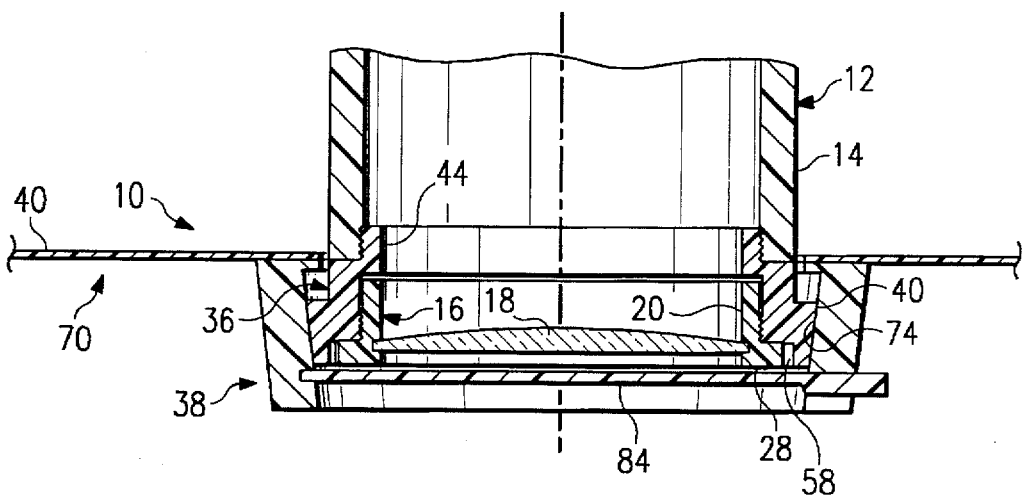
FIG. 5 is a sectional view of the system as installed on a microscope.

As most clearly shown in FIG. 5, the angle of the universal engagement surface 46 assures that the positioning member 38, when mounted upon the adapter member 36, will not interfere with the lens unit housing 14. There is also no interference between the positioning member 38 and the lens unit 16.

After a surgical procedure has been completed and removal of the microscope drape 70 is desired, the positioning member 38 is demounted from the adapter member 36 by, for example, accessing the major base end 66 and pulling the positioning member 38 away from the adapter member 36. The adapter member 36 can be retained in the lens unit housing 14 with the lens unit 16 to facilitate subsequent installation of a replacement microscope drape.

If the microscope drape 70 is to be used with a different microscope made by a different manufacturer that is of the same general size as the microscope 12, a different adapter member than the adapter member 36 must be provided. However, the difference between the adapter member 36 and the adapter member for a microscope of different manufacture lies solely in the characteristics of the threads 42 and 54, which must be matched with the microscope to assure compatible engagement of the adapter member with the microscope lens unit housing.

Adapter members for microscopes of different manufacturers can include external threads formed on the exterior step 48 or internal threads formed in the recess 58. However, the underlying common feature of all adapter members, regardless of differences in the thread characteristics and thread location, is the same identical engagement surface 46 for all adapter members.

Thus, microscopes made by different manufacturers of the same general size and shape, equipped with adapter members such as the adapter member 36, are capable of using the same microscope drape 70 having the same positioning member 38. The microscope drape 70 is thus a universal microscope drape and the positioning member 38 is a universal positioning member.

Some advantages of the invention evident from the foregoing description include a universal positioning system for a microscope drape that is adaptable to microscopes made by different manufacturers. The universal tapered engaging surfaces of the adapter member and the positioning member for the microscope drape ensure ease of application and ease of removal of the drape from the microscope. The tapered structure of the positioning member for the microscope drape also assures against any interference between the positioning member and the lens unit housing of the microscope. In addition, the universal tapered engaging surface of the microscope drape positioning member is relatively economical to manufacture. Users of the universal microscope drape will have a simpler task in maintaining inventory of microscope drapes. Furthermore, once an adapter member has been obtained for a particular microscope, it can be reused over and over again.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An assembly for positioning a microscope drape on a microscope, said microscope having thread means for detachably engaging thread means of a detachable lens unit, said assembly comprising, a) an adapter member formed of a rigid material, said adapter member having first thread means for detachably engaging the thread means of the microscope, said adapter member having second thread means for detachably engaging the thread means of the detachable lens unit, said adapter member having first tapered engaging means comprising an outer surface in the form of a conical frustum, and b) a drape positioning member formed of a flexible material, said drape positioning member having a major base end and a minor base end, said drape positioning member being attachable to a microscope drape, said drape positioning member having second tapered engaging means for detachably and primarily frictionally engaging the first tapered engaging means of the adapter member, said second tapered engaging means comprising an inner surface in the form of a conical frustum, said adapter member and said drape positioning member each having an annular configuration.

2. The drape positioning member of claim 1 further comprising a lip portion formed on said major base end of said drape positioning member for preventing complete disengagement of said drape positioning member and said adapter member.

3. A microscope drape positioning assembly for mounting a microscope drape on a microscope, said microscope drape positioning assembly comprising, a) a rigid adapter ring having a first thread means for engagement with the microscope and a second thread means for engagement with a detachable lens unit for the microscope such that the adapter ring can be interchanged with the lens unit and when interchanged can receive the removed lens unit at the second thread means to hold the lens unit in a functional viewing position on the microscope, and b) a flexible mounting sleeve attachable to the microscope drape, said mounting sleeve having a major base end and a minor base end, said mounting sleeve and said adapter ring having complementary, primarily frictionally engaging tapered surfaces for detachable securement of said mounting sleeve to said adapter ring, said mounting sleeve having an inside tapered surface in the form of a hollow conical frustum and said adapter ring having an outside tapered surface in the form of a conical frustum whereby the microscope drape that attaches to the mounting sleeve can be positioned on the microscope by frictionally engaging the mounting sleeve and the adapter ring after the adapter ring is interchanged with the lens unit.

4. The flexible mounting sleeve of claim 3 further comprising a lip portion formed on said major base end of said flexible mounting sleeve for preventing complete disengagement of said flexible mounting sleeve and said adapter ring.

5. An adapter member for positioning a microscope drape on a microscope comprising a rigid adapter ring having an exterior thread for engagement with a microscope and an interior thread for engagement with a detachable lens unit of the microscope such that the adapter ring can be interchanged with the lens unit at the interior thread to hold the lens unit in a functional viewing position on the microscope, said adapter ring having a tapered outside surface with an angle of taper ranging between about 15 degrees and about 22 degrees in the form of a conical frustum for primarily frictional engagement with a complementary inside tapered surface of a microscope drape mounting sleeve having a major base end and a minor base end, and being formed of a deformable thermoplastic material to permit detachable, frictional securement of the mounting sleeve to said adapter ring whereby a microscope drape cover member that attaches to the mounting sleeve can be positioned on the microscope by engaging the mounting sleeve and the adapter ring after the adapter ring is interchanged with the lens unit.

6. The microscope drape mounting sleeve of claim 5 further comprising a lip portion formed on said major base end of said microscope drape mounting sleeve for preventing complete disengagement of said microscope drape mounting sleeve and said adapter ring.

7. A microscope drape assembly comprising:
 a) a drape adapter having
  i) a first thread means for engaging thread means of a microscope,
  ii) a second thread means for engaging thread means of a lens unit, and
  iii) a tapered outer surface defining a drape engaging means in the form of a conical frustum;
 b) a flexible drape mounting ring having a major base end and a minor base end and having an inner surface in the form of a conical frustum for primarily frictionally engaging the drape engaging means of the drape adapter; and
 c) a microscope drape attached to the drape mounting ring.

8. The drape mounting ring of claim 7 further comprising a lip portion formed on said major base of said drape mounting ring for preventing complete disengagement of said drape mounting ring and said drape adapter.

* * * * *